(12) United States Patent
Rane et al.

(10) Patent No.: US 12,416,073 B2
(45) Date of Patent: Sep. 16, 2025

(54) PLASMA BASED SYSTEM FOR GENERATING ANTIMICROBIAL COATING ON FLEXIBLE POLYMERIC SUBSTRATES AND PROCESS THEREOF

(71) Applicant: INSTITUTE FOR PLASMA RESEARCH, Gandhinagar (IN)

(72) Inventors: Ramkrishna Rane, Gandhinagar (IN); Akshay Vaid, Gandhinagar (IN); Alphonsa Joseph, Gandhinagar (IN); N. I. Jamnapara, Gandhinagar (IN)

(73) Assignee: INSTITUTE FOR PLASMA RESEARCH, Gandhinagar (IN)

( * ) Notice: Subject to any disclaimer, the term of this patent is extended or adjusted under 35 U.S.C. 154(b) by 64 days.

(21) Appl. No.: 18/450,956

(22) Filed: Aug. 16, 2023

(65) Prior Publication Data
US 2024/0247364 A1 Jul. 25, 2024

(30) Foreign Application Priority Data
Jan. 19, 2023 (IN) .............................. 202321003767

(51) Int. Cl.
C23C 14/35 (2006.01)
A61L 15/42 (2006.01)
C23C 14/20 (2006.01)

(52) U.S. Cl.
CPC .............. C23C 14/35 (2013.01); A61L 15/42 (2013.01); C23C 14/20 (2013.01); A61L 2300/404 (2013.01)

(58) Field of Classification Search
CPC .................................................. C23C 14/34
(Continued)

(56) References Cited

U.S. PATENT DOCUMENTS 3,652,443 A * 3/1972 Fish .................... C10M 3/00
204/192.12
4,179,351 A * 12/1979 Hawton, Jr. ........ H01J 37/3405
204/298.21
(Continued)

FOREIGN PATENT DOCUMENTS

CN 113844140 A * 12/2021
EP 0 908 553 A2 4/1999
(Continued)

OTHER PUBLICATIONS

O.V. Abramov et al., "Pilot scale sonochemical coating of nanoparticles onto textiles to produce biocidal fabrics", Surface & Coatings Technology, vol. 204, 2009, pp. 718-722.
(Continued)

Primary Examiner — John J Brayton
(74) Attorney, Agent, or Firm — Merchant & Gould P.C.; Daniel J. Pereira (57) ABSTRACT

A cylindrical magnetron sputtering assembly for coating on a flexible polymeric substrates with an antimicrobial material, said assembly comprising a sputtering setup and a cylindrical magnetron assembly; said cylindrical magnetron assembly being mounted in said sputtering setup: wherein said cylindrical magnetron assembly comprises: at least one cylindrical anode with slots mounted on a top base plate; at least one central target cylindrical cathode positioned at the center of said anode; a mechanical assembly for moving plurality of said flexible polymeric substrates; said mechanical assembly comprising at least one winder, at least one unwinder, plurality of pulleys and plurality of motors; said sputtering setup comprising plurality of magnetic field coils, vacuum chamber and plurality of power supply. Also provided is process for producing antimicrobial coating on
(Continued)

flexible polymeric substrates by the cylindrical magnetron sputtering assembly.

20 Claims, 11 Drawing Sheets

(58) Field of Classification Search
USPC .................. 204/298.21, 298.24, 298.08
See application file for complete search history.

(56) References Cited

U.S. PATENT DOCUMENTS

| | | | |
|---|---|---|---|
| 6,368,361 | B1 | 4/2002 | Yayabe et al. |
| 8,070,918 | B2 * | 12/2011 | Suzuki ................ D06M 11/83 |
| | | | 204/192.15 |
| 2003/0056297 | A1 | 3/2003 | Sun |
| 2003/0088923 | A1 | 5/2003 | Sivik et al. |
| 2003/0106162 | A1 | 6/2003 | Scheper et al. |
| 2008/0193496 | A1 | 8/2008 | Gabbay |
| 2022/0380890 | A1 * | 12/2022 | Danziger ............. C23C 16/545 |

FOREIGN PATENT DOCUMENTS

| | | | | |
|---|---|---|---|---|
| EP | 1 490 543 | A2 | | 12/2004 |
| EP | 2 104 763 | A1 | | 9/2009 |
| EP | 2 294 260 | A1 | | 3/2011 |
| EP | 2 848 718 | A1 | | 3/2015 |
| EP | 3095891 | A1 * | 11/2016 | ........... C23C 14/205 |
| EP | 3 227 490 | A1 | | 10/2017 |
| KR | 20150012139 | A * | 2/2015 | |
| WO | 00/75415 | A1 | | 12/2000 |
| WO | 03/080911 | A2 | | 10/2003 |
| WO | 2004/050132 | A2 | | 6/2004 |
| WO | 2011/073697 | A1 | | 6/2011 |
| WO | 2015/023644 | A2 | | 2/2015 |
| WO | 2016/087864 | A1 | | 6/2016 |

OTHER PUBLICATIONS

M. Amberg et al., "Design, characterisation and operation of an inverted cylindrical magnetron for metal deposition"; Plasma Devices and Operations, vol. 12, No. 3, Sep. 2004, pp. 175-186.

C. Castro et al., "Structure-reactivity relations for DC-magnetron sputtered Cu-layers during *E. coli* inactivation in the dark and under light", Journal of Photochemistry and Photobiology A: Chemistry, vol. 216, 2010, pp. 295-302.

Ying-Hung Chen et al., "Antibacterial silver coating on poly(ethylene terephthalate) fabric by using high power impulse magnetron sputtering", Surface & Coatings Technology, vol. 232, 2013, pp. 868-875.

D. Hegemann et al., "Recent developments in Ag metallised textiles using plasma sputtering", Materials Technology, 2009, vol. 24, No. 1, pp. 41-45.

M. A. Keller et al., "Continuous coating of synthetic fibers using Hexamethyldisiloxane", Plasma Process. Polym., 2007, vol. 4, pp. 1063-1067.

L. Surdu et al., "Research regarding the cover factor of magnetron sputtering plasma coated fabrics", Industria Textila, 2019, vol. 70, No. 2, pp. 154-159.

J. Scholz et al., "Investigations on fabrics coated with precious metals using the magnetron sputter technique with regard to their anti-microbial properties", Surface & Coatings Technology, vol. 192, 2005, pp. 252-256.

* cited by examiner

Fig. 1 Schematic of cylindrical magnetron sputtering system

(a) Staphylococcus Aureus (b) Escherichia Coli

PLASMA BASED SYSTEM FOR GENERATING ANTIMICROBIAL COATING ON FLEXIBLE POLYMERIC SUBSTRATES AND PROCESS THEREOF

RELATED APPLICATION

The present application is a direct U.S. National Application which claims priority to Indian Application No. IN 202321003767 filed Jan. 19, 2023.

FIELD OF THE INVENTION

The present invention relates to medical science and general health. More specifically the present invention relates to medical textile like bandages, sterile gauzes, antiseptic wipes; air/water filter media such as polypropylene, polyeurethane/polyethylene, nylon, cotton etc.

BACKGROUND AND THE PRIOR ART

In spite of many technical advances in medical science and general health, microbial infections remain a major problem worldwide. In the field of medical textile, controlling the growth of virus and micro-organisms such as bacteria, fungi on the textile surface is important such as in case of bandages/dressings etc. Considering the present pandemic times, need of air purification media such as filter elements/filter media having anti-microbial properties has increased. Usually, different techniques such as Ethylene oxide (ETO) treatment and other sterilization media are used to control the growth of micro-organisamas which can limit the spread of infections. But this is one time sterilization. The growth of microbial species (bacteria/fungi etc.) result in delayed recovery of patient or sometimes medical complications in specific cases with comorbidity. Usually, dressings upto certain time are disposed off as medical waste or sterilized in autoclave. As a solution, one such method is the surface modification of textile via a coating deposition method to provide antimicrobial/antiviral properties on the surface. These antimicrobial fabrics can be used in clothing such as surgical garments and in dressings such as sterile gauzes, antiseptic wipes, bandages. This helps to prevent the growth of bacteria/pathogenic microorganisms and therefore reduces the probability of infections. Similarly, such antimicrobial coatings are also required in air purification media where microbial species of bacteria, fungi etc. often get collected/filtered and pose a threat of microbial growth. Some coatings made up of copper and silver which exhibit antimicrobial properties have been used for many years. These metals are capable in reducing the growth of a wide spectrum of micro-organisms. Even the deposition of thin metallic layer (i.e. less than 100 nm) on the textile surface prevents growth of micro-organisms. Such antibacterial cloths having metallic coated film or particles are known as medical textile.

Prior art indicates that chemical methods have been developed to produce antimicrobial surfaces of yarns (threads) and fabrics. The most common method was impregnating nanoparticles of metal oxide where the metal oxide nanoparticles are loaded onto the fabrics by immersing the fabric into the aqueous solution of one or two metals (WO 2016/087864). Another method was by using conventional melt spinning manufacturing technique where silver and copper salts were used (WO 2015023644). Coating of silver nanoparticles in the nanometer range using a chemical method has been described in EP1490543. WO03/080911 further describes an antimicrobial yarn using a coating of silver nanoparticles and method for manufacturing which involves soaking of yarns in the Nano silver solution. The antimicrobial fabrics are then made by knitting these yarns. In case of yarn, it was observed that, the coating of nanoparticles like silver was not adhered properly due to the pretreatment process. Hence, a new pre treatment method on precious yarn was also proposed for producing antimicrobial fabrics (WO2011/073697). The method for increasing the adhesion as well as uniformity of the nanoparticle to the fabric during the process of impregnation is proposed in EP3227490. The invention related to the system for preparing antimicrobial fabrics coated with zinc oxide nanoparticle using sono chemical method as described in EP2294260. It is known from the above mentioned prior art survey as well as from U.S. Pat. No. 6,368,361, EP908553, WO2004/050132, US2003/0056297, US2003/0106162, and US2003/0088923 that the antimicrobial substance is typically applied from solution by wet processing techniques.

Physical and chemical vapor deposition methods have also been developed to produce antimicrobial yarns and fabrics. The invention related to a process in which an antimicrobial coating is prepared on the surface of a substrate using a plasma treatment is detailed in EP2104763 where plasma polymersiation process (a chemical vapour deposition process) is used. In this process, chemicals based on aromatic heterocycle are polymerized to form antimicrobial active compound on the substrate.

WO00/75415, EP2848718, EP1490543, US2008/0193496 discloses antibacterial fabric/yarn/fabric by using chemical methods like sonochmeical method, dip coating method, electolytic deposition, melt spinning manufacturing method. However the wet processing techniques have the disadvantage that they are relatively environmentally unfriendly, since large amounts of chemicals and solvents are required. In order to address the limitations of such prior art, various attempts have been made by different researchers to use physical vapor deposition techniques like plasma based magnetron sputtering to modify the surface of textile materials like non-wovens and knitted fabrics.

Some of the previous studies have reported the deposition of metal and metal oxide nanoparticles on nylon, polyester and cotton fabrics to give them antibacterial properties [Abramov et al, *Surface & Coatings Technology* 204 (2009) 718-722]. Scholza et al., *Surface & Coatings Technology* 192 (2005) 252-256 tested silver, gold, platinum, platinum/rhodium, and copper coatings deposited on textile fabric by using planar magnetron sputtering and then compared them in terms of their binding strength and antimicrobial properties.

Castro et al. (*Journal of Photochemistry and Photobiology A: Chemistry* 216 (2010) 295-302) studied the application of copper (Cu) by using DC magnetron sputtering for the inactivation of *Escherichia coli* on cotton fabrics. Chen et al (*Surface & Coatings Technology* 232 (2013) 868-875) used high-power pulsed magnetron sputtering method for depositing silver coating on the surface of a PES fabric in such a way that the fabric was evenly coated and a good adhesion of silver coating to the substrate was achieved. Further, Chen et al. worked for obtaining a brass coating on the same textile fabric by using the physical vapor deposition technique. An antibacterial and corrosion-resistant brass coating was produced on the PET fabric.

Abramov et al, Scholza et al, Castro et al., Chen et al discloses plasma based planar magnetron sputtering for antibacterial coating on fabric, but have limitations to do uniform coating on the yarn.

Most of the researchers have used planar magnetron sputtering for coating on fabric. However, in case of woven fabric, the uniform deposition on all the surfaces of fibers is an issue. The only top surface of the fabric gets coated while the surface of overlapping knitted yarns is not coated. Lilioara et al, reported in their work that the uniform coating on all the yarns was not observed using planar magnetron sputtering method. It was also shown that the cover factor of the fabric decreases after copper coating (Lilioara et al, *industria textila,* 2019, Vol-70, No. 2)

Thus the planar magnetron sputtering allows the deposition on a flat surface, but have limitations to do uniform coating on yarn surfaces.

Hegemann et al. (*Materials Technology* (2009) VOL 24 NO 1, 41-45) developed a plasma sputtering process, which deposits a nanometer thick metal film of Ag onto textile fibres or yarn in a continuous process. This fibre coater is equipped with an inverse cylindrical magnetron sputtering, where the fibres are directed several times through the plasma zone enabling a uniform coating [Amberg et al., *Plasma Devices and Operations,* 2004, 12:3, 175-186]. Additionally, plasma cleaning/activation and plasma polymerisation processes can be realised in the same reactor [Keller et al, *Plasma Process. Polym.* 2007, 4, S1063-S1067]. The fibres are wind up and off in air at velocities up to 100 m/min by using conventional rolls and are transported through a sealing system into the vacuum chamber.

Hegemann et al., Amberg et al, Keller et al discloses inverted cylindrical magnetron which is able to uniformly coat the moving yarn. In this process the cathode is the target material and is a hollow cylinder with a large diameter. In such a case, it is difficult to use large diameter cathode as it is too expensive for materials like silver, gold and copper. In addition it is difficult to provide uniform water cooling to such large diameter cathode.

There is a need for a coating means as well as method that can deposit antimicrobial material on the yarn as well as fabric surface (woven or non-woven) in a single system.

As mentioned above various process for providing antibacterial coatings are known but all have some disadvantages. It has been found that the wet processing techniques have the disadvantage that they are relatively environmentally unfriendly, since large amounts of chemicals and solvents are required and high energy costs are involved for heating and drying process. In addition, some wet deposition processes are difficult to scale-up due to the complicated multi-step processing. Thus there is a need for a dry technique for making antimicrobial coatings.

Secondly the plasma based technique is an environmentally friendly process. However the previous study indicates that, most of the researchers have used plasma based planar magnetron sputtering for coating on fabric which is suitable for planar substrates. However, in case of woven fabric, the uniform deposition on all the surfaces of fibers is an issue where the top surface of the fabric which is exposed to plasma gets coated while the surface of overlapping knitted yarns is not coated. The planar magnetron sputtering allows the deposition on a flat surface, but have limitations to do uniform coating on the yarn. Lilioara et al, reported in their work that the uniform coating on all the yarns was not observe using planar magnetron sputtering method. It was also shown that the cover factor of the fabric decreases after copper coating (Lilioara et al, *industria textila,* 2019, Vol-70, No. 2)

Thirdly though the inverted cylindrical magnetron is able to uniformly coat the moving yarn, the cathode which is the target material is a hollow cylinder with a large diameter. It would be difficult to use this configuration as it would be too expensive for materials like silver, gold and copper. In addition it is difficult to provide uniform water cooling to such large diameter cathode.

Fourthly the planar magnetron sputtering is used for coating stationary or moving planar substrates like fabric while cylindrical magnetron is suitable for stationary or moving cylindrical substrates like yarn. However there does not exist a system which has provision to deposit both type of substrates in one apparatus.

Thus there is a need for deposition of antimicrobial coating on moving yarn(thread) as well as moving fabric in same system.

Object of the Present Invention

It is an objective of the present invention to overcome the drawbacks of the prior art.

It is another objective of the present invention to provide a non chemical (dry) method for producing uniform antimicrobial coatings on a moving yarn and woven/non-woven fabric.

It is a further objective of the present invention to provide a method which is a post cathode plasma based cylindrical magnetron sputtering process which can do antimicrobial coating on the textile yarn and woven/non-woven fabrics in an environment friendly manner.

BRIEF DESCRIPTION OF ACCOMPANYING FIGURES

FIG. 2 illustrates the details of each part of cylindrical magnetron assembly in accordance with the present invention. FIG. 2*a* shows the cylindrical magnetron assembly in isometric view while

SUMMARY OF THE INVENTION

Accordingly the present invention provides a cylindrical magnetron sputtering assembly for coating on a flexible polymeric substrates with an antimicrobial material, said assembly comprising a sputtering setup and a cylindrical magnetron assembly:

said cylindrical magnetron assembly being mounted in
said sputtering setup; wherein
said cylindrical magnetron assembly comprises:
at least one cylindrical anode with plurality of slots
mounted on a top base plate;
at least one central target cylindrical cathode positioned at
the center of said anode;
a mechanical assembly for moving plurality of said flexible polymeric substrates;
said mechanical assembly comprising at least one winder,
at least one unwinder, plurality of pulleys and plurality
of motors;
said sputtering setup comprising plurality of magnetic
field coils, vacuum chamber and plurality of power
supply.

According to another aspect of the present invention there
is provided a process for producing antimicrobial coating on
a flexible polymeric substrates by the cylindrical magnetron
sputtering assembly, said process comprising the steps of:
a) generating a low pressure plasma in the cylindrical
anode to sputter out an antimicrobial material from the
target cylindrical cathode,
b) generating magnetic field by said magnetic field coils
to increase electron density for sputtering,
c) performing an unwinding and a winding spool mechanism with said motors inside said vacuum chamber,
d) moving said flexible polymeric substrates multiple
times through said cylindrical magnetron assembly to
deposit a coating of said antimicrobial material of
thickness of 50-100 nm.

DETAILED DESCRIPTION OF THE PRESENT INVENTION

The present invention provides a non chemical method for
the deposition of antimicrobial material on yarns and fabric
(woven and non-woven both) using plasma based cylindrical
magnetron sputtering technique having post cathode configuration which can uniformly coat a moving yarn as well
as moving fabric.

The present inventors have found a post cathode (i.e.,
inner cathode and outer anode) cylindrical magnetron sputtering assembly to deposit a uniform, thin antimicrobial
coatings on a moving yarn or woven/non-woven fabric
surface. The cylindrical magnetron sputtering assembly can
be used for coating antimicrobial material selected from
copper, zinc, and titanium; preferably nano copper oxide.

The cylindrical magnetron sputtering assembly in accordance with the present invention is used for coating on a
flexible polymeric substrates with an antimicrobial material.
The assembly comprises a sputtering setup and a cylindrical
magnetron assembly:
said cylindrical magnetron assembly being mounted in
said sputtering setup;
wherein
said cylindrical magnetron assembly comprises:
at least one cylindrical anode with plurality of slots
mounted on a top base plate;
at least one central target cylindrical cathode positioned at
the center of said anode;
a mechanical assembly for moving plurality of said flexible polymeric substrates; said mechanical assembly
comprising at least one winder, at least one unwinder,
plurality of pulleys and plurality of motors;
said sputtering setup comprising plurality of magnetic field
coils, vacuum chamber and plurality of power supply.

The modified cylindrical magnetron sputtering assembly
is specifically designed to coat both moving fabric (both
woven and non-woven) as well as moving yarn with antimicrobial material. The slots are made in anode through
which fabric is passed in vertical direction while yarn is
passed in the anode volume in horizontal direction. The
coating process has been developed so as to deposit controlled thickness in nanometer range (50-100 nm) of copper
oxide on moving yarn and fabric (woven/non-woven). This
coating has very good adhesion with substrate. No bacterial
growth is observed on the coated surface of the yarn. Further
the viral load on the coated surface was reduced significantly
(3 Log reduction).

A novel mechanical assembly configuration in accordance
with the present invention comprises a fixture specifically
designed to accommodate both yarn and fabric (in roll-to-roll concept); in combination with a modified cylindrical
magnetron sputtering setup. The assembly, comprises of a
special arrangement involving a static cylinder with known
slots/gap areas for the moving substrate to pass through; so
that maximum utilization of the sputtered material is done
and thereby efficient use of space/chamber volume is done.
This unique arrangement also prevents other components of
the chamber to be coated with substrate, thereby reducing
the chamber cleaning/maintenance loads. The above
mechanical assembly when operated in vacuum ($10^{-2}$ mbar-$10^{-1}$ mbar) and in combination with a DC power supply
connected to the cylindrical magnetron operating in the
range of −600 to −800 Volts under specific gas environment
such as argon, oxygen etc, results in deposition of coating of
metal oxides having nanometer range thickness on polymeric substrates.

Figure 3:
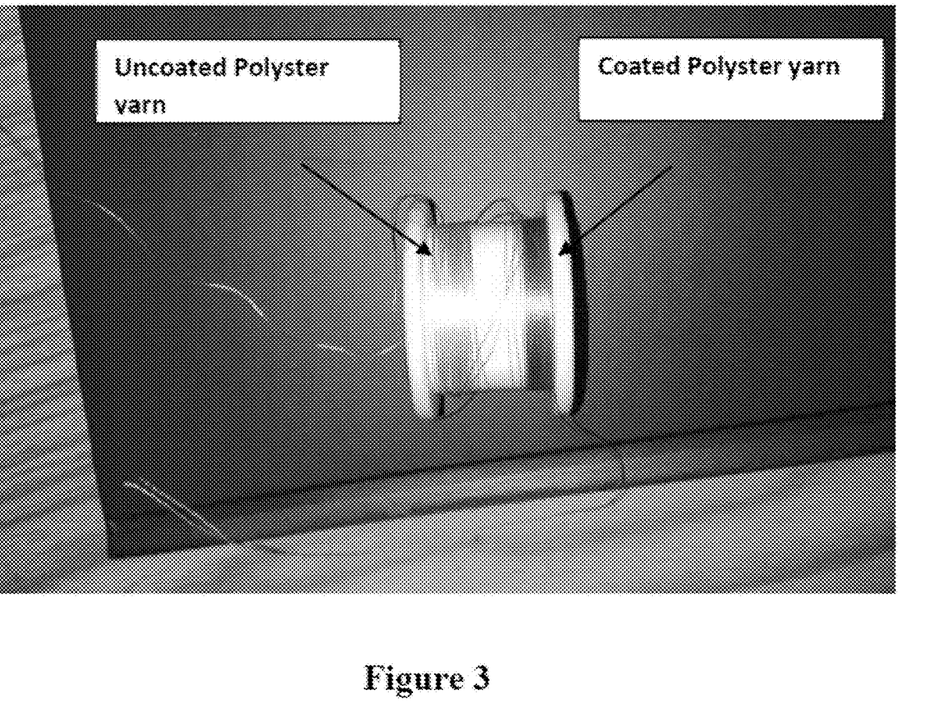
FIG. 3 illustrates the coated and uncoated polyester yarn.
Figure 4:
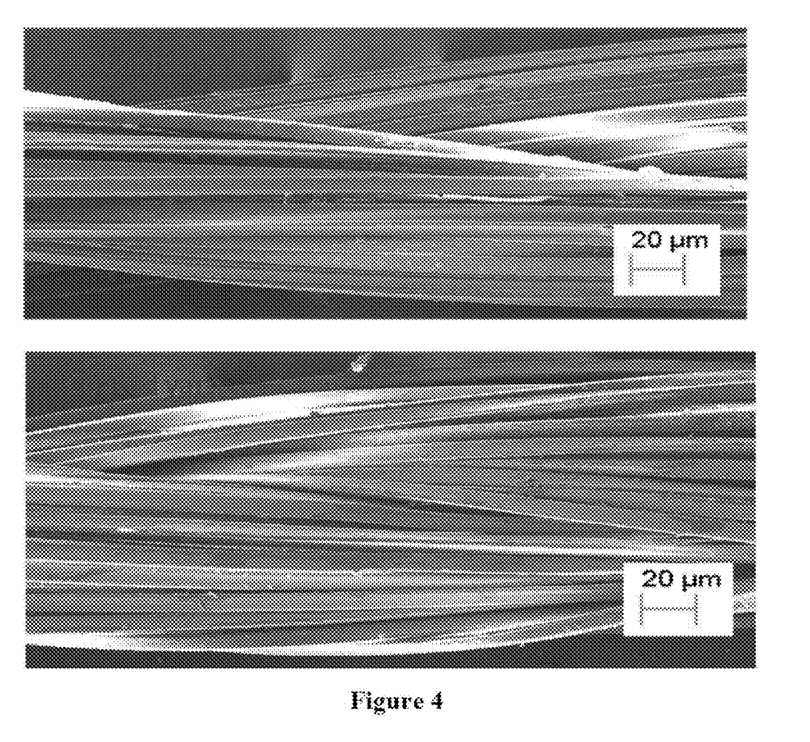
FIG. 4 illustrates the uncoated and copper oxide coated polyester yarn showing multiple filaments in the single yarn.
Figure 5:
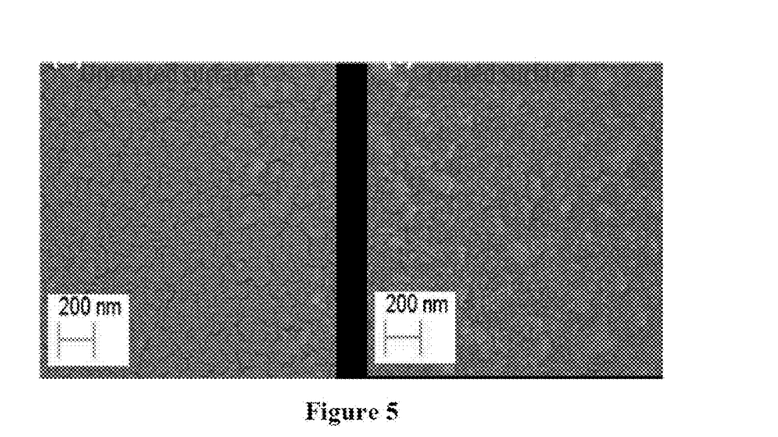
FIG. 5 illustrates the surface of the single filament (uncoated and coated) showing the presence of nano copper oxide.
Figure 7:
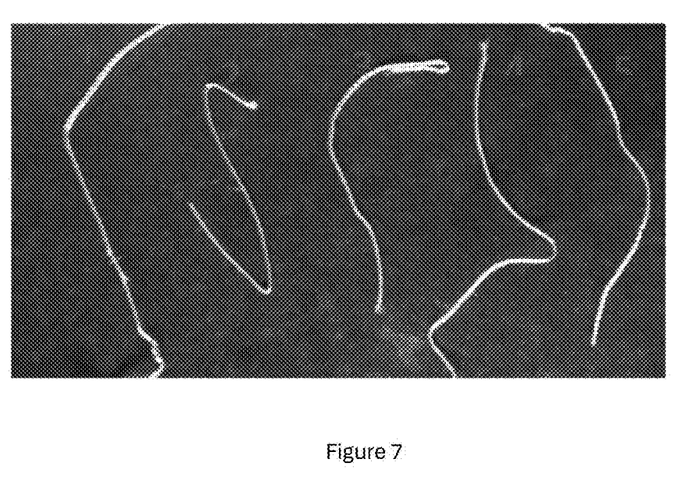
FIG. 7 illustrates the images of (1) Uncoated (2) Coated as it is (3) After 1 wash (4) After 2 wash and (5) After 4 wash.

The coating process provides a deposit of nano thickness
(50-100 nm) of copper oxide on moving polyester yarn.
(FIG. 1 to FIG. 3) wherein the speed of yarn would be in the
range of 0.5 to 2 metre per minutes. The present inventors
have found that the coating was uniform. (FIG. 4 and FIG.
5). It had good adherence with the substrate. (FIG. 7 and
Table-1)

Figure 8:
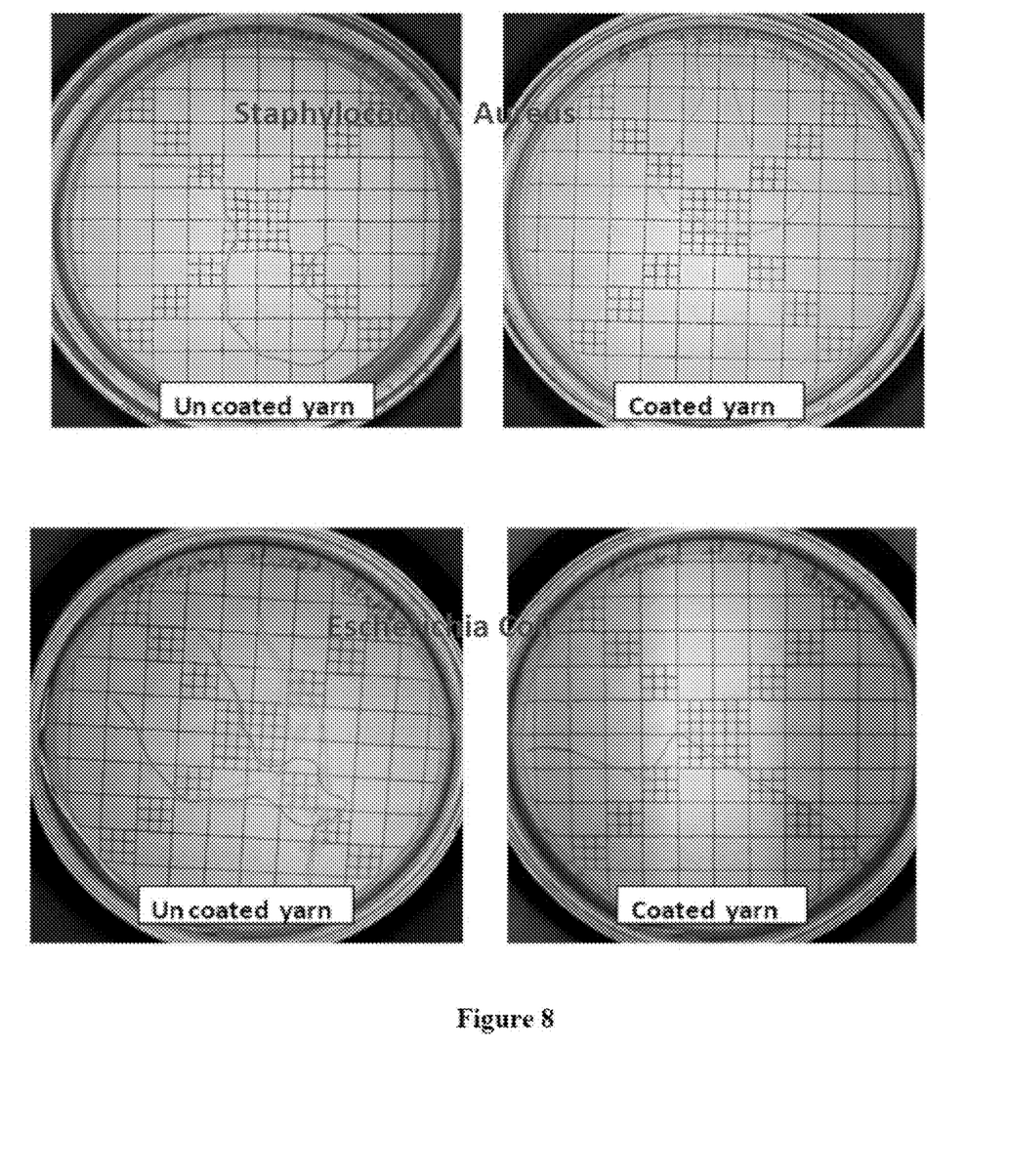
FIG. 8 illustrates the growth of (a) *Staphylococcus Aureus* and (b) *Escherichia Coli.*
Figure 9:
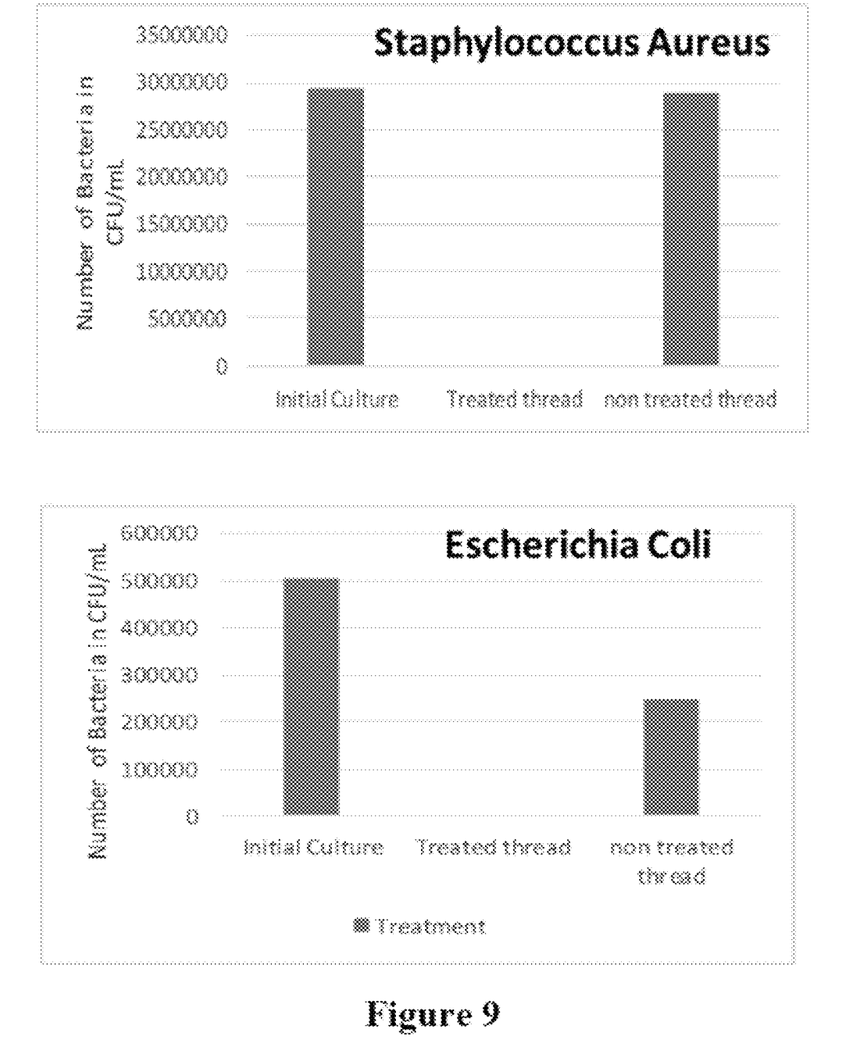
FIG. 9 illustrates the number of bacteria in culture for (a) *Staphylococcus Aureus* and (b) *Escherichia Coli.*
Figure 10:
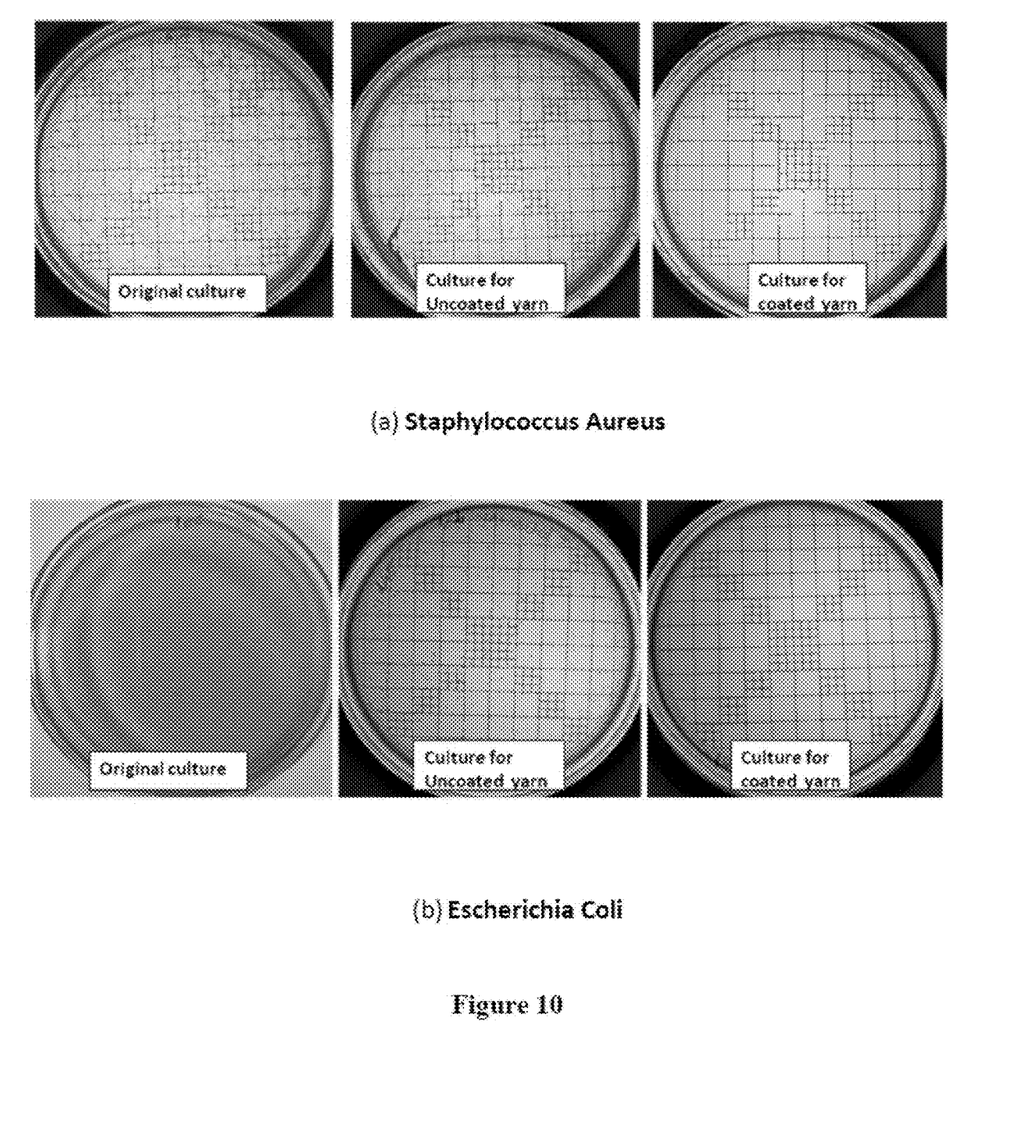
FIG. 10 illustrates the growth of the bacterial ((a) *Staphylococcus Aureus* and (b) *Escherichia Coli*) in the plates which are incubated after removal of yarns.
Figure 11:
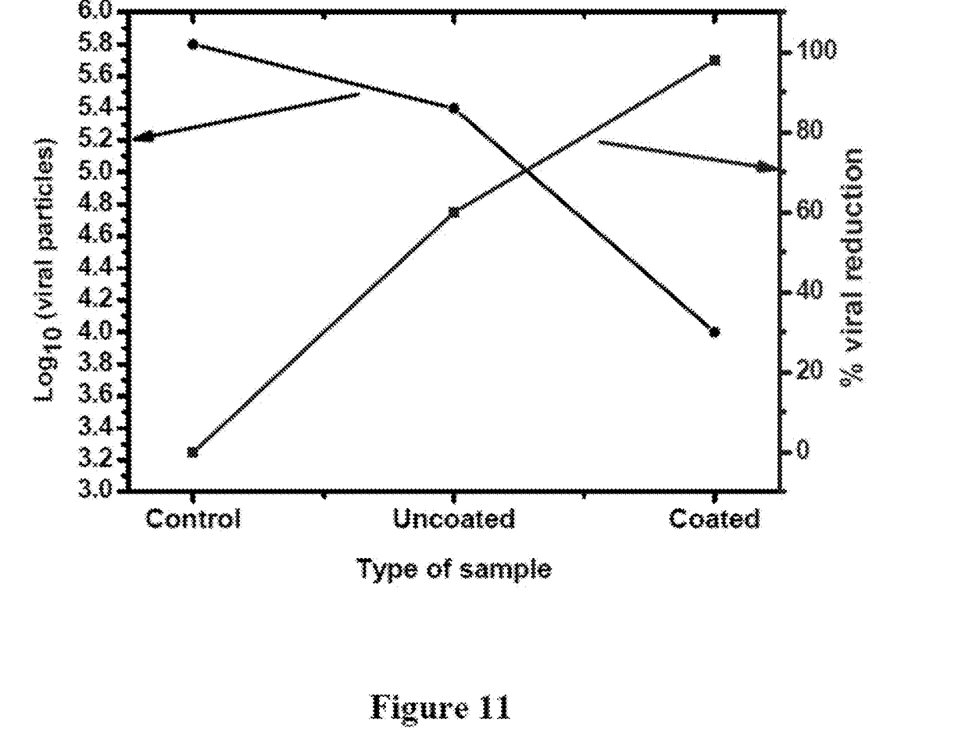
FIG. 11 illustrates the number of viral particles and percentage viral reduction for uncoated and coated samples.

The antimicrobial activity of copper oxide coatings (50-100 nm) deposited by cylindrical magnetron sputtering in
accordance with the present invention on polyester yarn
were tested for bacterial growth and show no growth of
*Staphylococcus Aureus* and *Escherichia Coli* bacteria. (FIG.
8 to FIG. 10 and Table-3). The copper oxide coating was also
tested for viral reduction studies using SARS-Cov-2. The
coated sample shows >97% viral reduction (FIG. 11)

The post cathode based cylindrical magnetron sputtering
in accordance with the present invention is most suitable as
it provides uniform and adherent coating on yarn surface.
Moreover the target material here is the cathode and is in the
form of a small rod or tube which is cost effective. The water
cooling can be provided easily to the cathode in post cathode
configuration. In accordance with the present process the
cold water can enter from one end of the tubular cathode and
flow through the other end which ensures uniform cooling of
the cathode.

The present method of deposition of antimicrobial coating
on moving fabric (both woven and non-woven) as well as
moving yarn is environment friendly and coating covers the
complete surface area of the yarn. The main advantage of
this method is to deposit thin coatings on cylindrical textile
substrates like yarn.

The coated yarn prepared by the assembly of the present
invention shows antimicrobial properties. The yarn is coated
with antimicrobial material by using environment friendly
dry technique compared to other wet chemical processes.

Additionally copper/copper oxide material is used as antimicrobial which is cheaper compared to conventionally used silver material. The yarn is effective against bacteria and virus (like covid-19) The uniqueness and novelty of the present invention over the prior art resides in its capability to handle both yarn and fabric (woven & non-woven) in the same system without changing anything in the coating system. These yarn can be used to make fabric, medical bandages/dressing gauges as well as antimicrobial, antiviral filters. These antimicrobial fabrics can be used in clothing such as surgical garments, and in dressings such as bandages etc, which are of single use type.

Additionally, such anti-microbial coating can also be generated on flexible polymeric filter media substrates such as polypropylene, polystyrene, polyethylene, cotton etc. for air and water purification purposes. Thus, this can be a very important product and process for anti-microbial filter media (air and water purification purposes).

DETAILED DESCRIPTION OF ACCOMPANYING DRAWINGS

Figure 1:
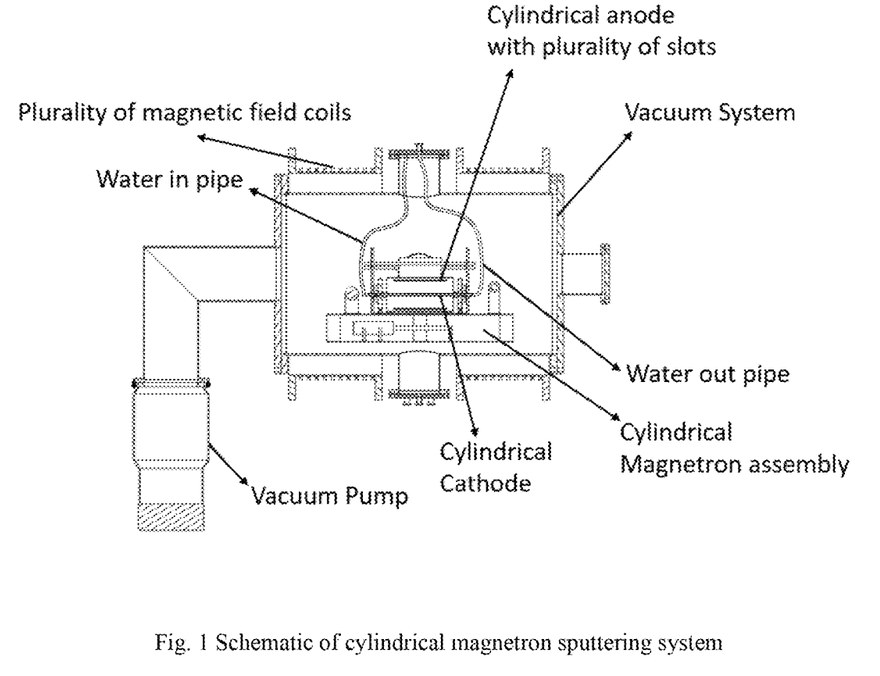
FIG. 1 illustrates the post cathode cylindrical magnetron sputtering setup in accordance with the present invention.
Figure 2A:
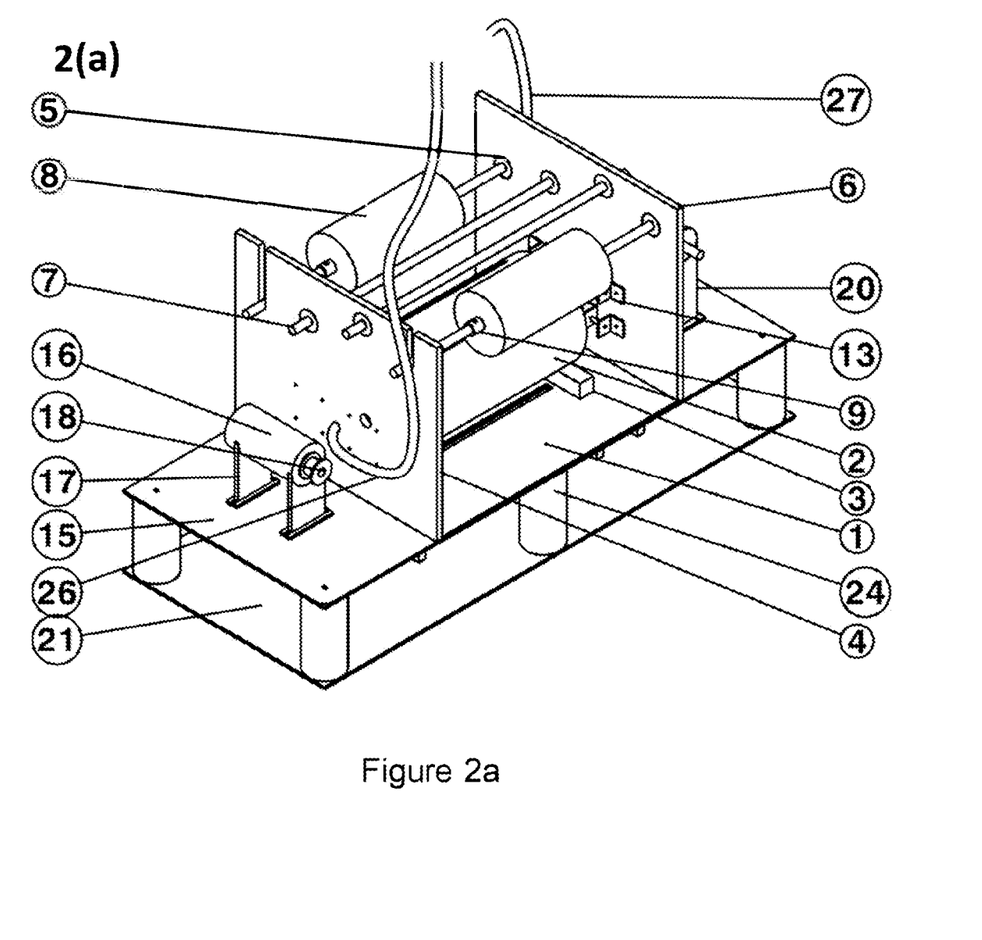
Figure 2B:
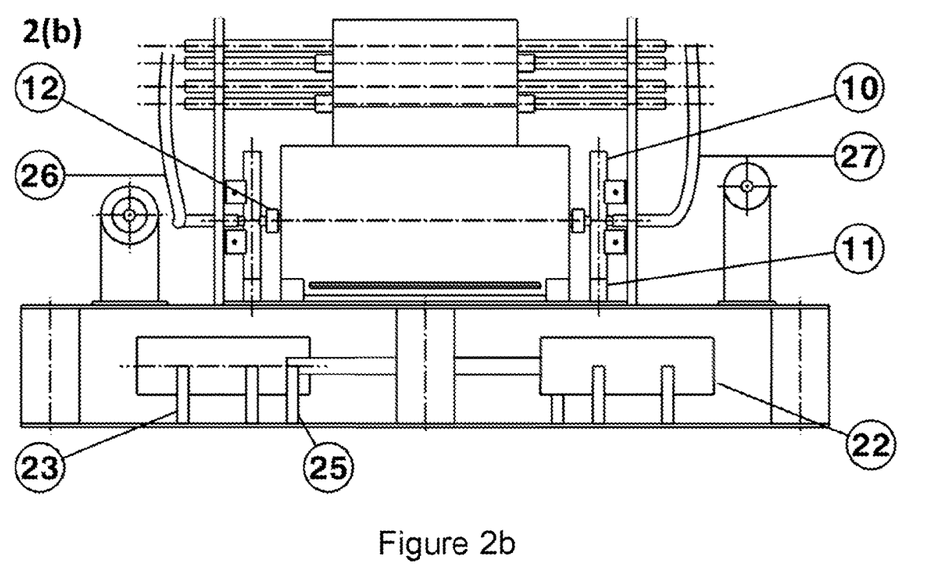
FIG. 2*b* shows front view and FIG. 2*c* shows top view.
Figure 2C:
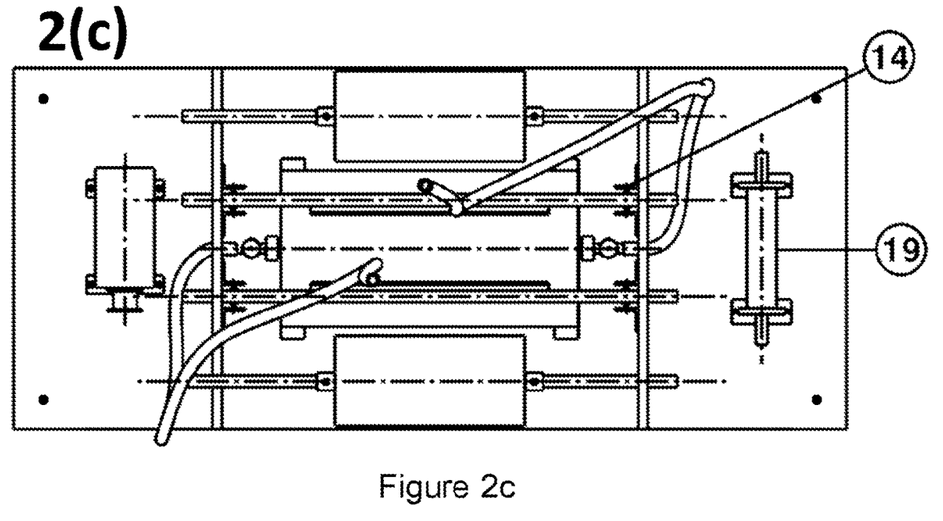

In accordance with the present invention, in order to carry out the deposition of antimicrobial material, a post cathode cylindrical magnetron sputtering setup (FIG. 1) is used. The FIG. 1 shows the schematic of cylindrical magnetron sputtering system having magnetic field coils and magnetron assembly. The cylindrical magnetron assembly for depositing copper oxide on substrates (yarn and woven or non-woven fabrics) is mounted in the sputtering setup. This would include a winder and an unwinder for cases where the substrates (yarns and fabrics) are in wound/roll form. The details of each part of cylindrical magnetron assembly is shown in FIG. 2.

The hollow stainless steel outer cover (part no. 2 of FIG. 2) called as cylindrical anode is mounted on a top base plate (part no. 15 of FIG. 2) using holders (part no. 3) for cylindrical anode. This cylindrical anodes have two slits to enter the fabric and two slits to exit the fabric. The central cylindrical copper pipe is used as a cathode (part no. 12) which sputters out copper in radial direction. The copper target pipe (part no. 12 of FIG. 2) is positioned at the center of the anode and is held with two supporting rods at the end. The water carrying tubes are connected to two end of copper target (part no. 26 and 27). The copper target is electrically isolated from the supporting metal rods by using insulating material such as Polytetrafluoroethylene (PTFE) or vacuum compatible polymers/ceramics (part no. 10 and 11). The two end plates (part no. 4 and 6) contain 04 pulleys (part no. 14 of FIG. 2) each to guide the yarn. The pulleys are fixed to end plates using L-bend (part no. 13). At one left end of the base plate, the motor for winding of the yarn (part no. 16 of FIG. 2) is mounted while at the other end, unwinder assembly (part no. 19 and 20 of FIG. 2) is mounted. The bobbin (part no. 18) for collecting the coated yarn (winder in case of a fabric) is connected to the shaft of the motor. On the right hand side, the spool of the yarn is mounted on the unwinder. The yarn from the unwinder enters in the hollow stainless steel cover through the pulley. The yarn passes through the volume between central target and outer steel cover. The yarn passes four times in the gap between central target and outer cylinder. When the yarn passes in this gap, the sputtered atoms from the central sputtering target gets deposited on the yarn. After deposition, the yarn comes out at another end where winding motor is mounted. The roller connected to the motor winds the yarn depending upon the speed of the motor.

The coating on fabric can also be made in the same system. The two bobbins (winder and unwinder) containing the (woven or non-woven) fabric are mounted in the system. The part no. 8 an 9 shows the bobbin and stopper. The fabric from the bobbin then enters in the cylindrical anode after sliding on the horizontal rod (part no. 7). The bobbin and rods are mounted on the plates using bearings (part no. 5). The fabric enters in the hollow anode from top side and exists at the bottom side of the anode. The drive motors (part no. 22) for winding of the fabric are mounted at the bottom on the bottom base plate (part no. 21). The motors are mounted on the bottom base plate using motor fixtures (part no. 23). The bottom plate and bottom base plate are separated through fixtures between two plates (part no. 24).

Once the spool of the yarn/fabric is connected to the sputtering assembly, it is placed in a cylindrical vacuum chamber as shown in FIG. 1. After evacuation of the vacuum chamber with rotary pump to a pressure of about $1 \times 10^{-2}$ to $9 \times 10^{-3}$ mbar, gas mixture of Argon: Oxygen in a pre-defined ratio (involving 5% to 20% Oxygen) is filled in the chamber to a pressure of about 0.1 to 1 mbar. The magnetic field of around 50 to 250 Gauss is applied in between the sputtering target and outer cylindrical cover. The Helmholtz coils which generate magnetic field are placed outside the vacuum chamber. A negative voltage of about −600 V to −800 V is given from a DC or pulsed DC power supply to the central sputtering target. As a consequence, a glow discharge plasma is formed in the gap between the sputtering target and outer cylindrical cover. The another DC power supply is connected to motor. The speed of the motor can be controlled in the range of 0.5 mtr/min to 2 mtr/min. The yarn/fabric passes through the plasma zone and gets coated. The coated yarn is collected on the winder bobbin of the motor. Similarly coated fabric is collected on the winder roller connected to motor at the bottom.

The present invention is now being illustrated by non-limiting examples.

Example 1: Deposition of Copper Oxide on Polyester Yarn

The multifilament polyester yarn of about 200 micron diameter is taken. The spoon of the yarn was mounted on the unwinder. The yarn is passed four times in the region between copper target and outer cylindrical cover. The yarn is collected on the shaft of the motor, which is placed at the other end. The assembly is placed in the vacuum chamber. The base pressure of $5 \times 10^{-2}$ mbar was achieved by using rotary pump. The operating gas argon and oxygen was introduced in the chamber up to the pressure of 0.1 mbar. The magnetic field of 200 Gauss was applied by passing current through Helmholtz coil. The copper target was given −800 V bias with reference to outer cylindrical cover. The DC voltage of 27 V was applied to the motor due to which the linear speed of the yarn was 0.5 mtr/min. The total residence time of the yarn inside the plasma region was one minute.

The yellow color of copper oxide nano film was observed on the yarn. The FIG. 3 shows coated and uncoated polyester yarn.

Example 2: SEM and EDAX of Coated and Uncoated Yarn

Figure 6A:
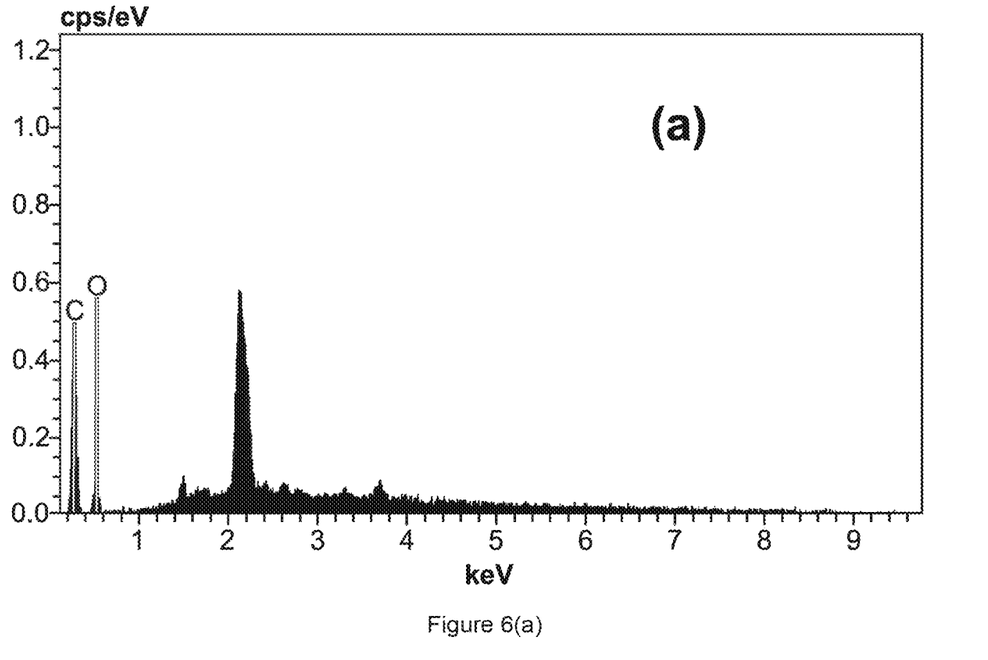
FIG. 6 illustrates the EDX spectra of (a) Uncoated and (b) Copper oxide coated polyester yarn.
Figure 6B:
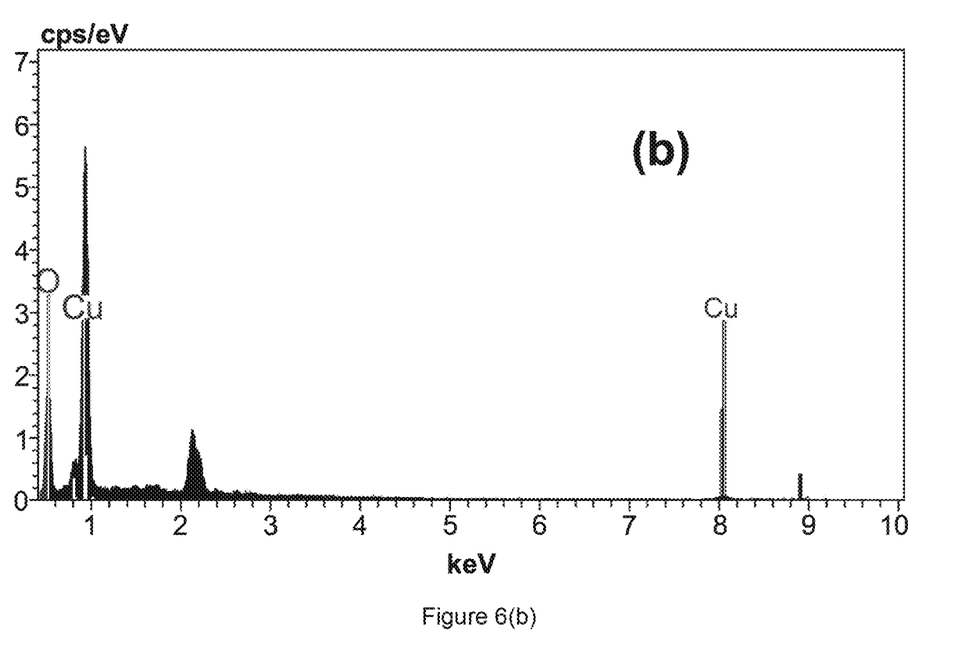

Small pieces of coated and uncoated polyester yarn were cut. The yarns were observed under High resolution Scanning Electron Microscope. All the multifilaments of the single yarn shows the deposition of nano copper oxide on the surface as shown in FIG. 4. Further the surface was observed under higher magnifications. The coated surface shows small grains of copper oxide deposited on the surface. (FIG. 5). The presence of copper and oxygen in the coated surface is confirmed by EDAX measurement. The EDAX spectra shown in FIG. 6 shows presence of copper in the coated specimen.

Example 3: Effect of Washing Yarn in Water

The copper oxide coated polyester yarn was dipped in water for 1 hour. This was considered as one wash. Then the copper percentage was measured by using EDX measurement. Similarly the measurement was done after 2 and 4 washes. The FIG. 7 shows images of washed yarns.

TABLE 1

Wt % of copper remaining after wash in water

| Type of yarn | Uncoated | Coated (No wash) | Coated (1wash) | Coated (2wash) | Coated (4wash) |
|---|---|---|---|---|---|
| Sample No | 1 | 2 | 3 | 4 | 5 |
| % of copper (wt %) | — | 15 | 10-11 | 8-9 | 5-6 |

Example 4: Testing of Yarn for Anti-Bacterial Efficacy

The anti-bacterial efficacy is tested for the below mentioned two types of bacteria 1. *Staphylococcus Aureus*.
2. *Escherichia Coli*.

The same protocol has been adopted to for both organism as described below:

1. Culture Preparation:

Bacteria is cultured taking culture in 10 mL of sterile Nutrient Broth and incubated for overnight (approximately 18 hours) at 37° C. Nutrient broth is removed by centrifugation and 10 mL of phosphate buffered saline (PBS) solution is added to have the bacterial plate. PBS suspended solution is diluted by adding more PBS solution till the optical density of prepared culture suspension is comparable to McFarland standard of 0.5. The prepared solution is considered as the stock culture. In order to determine the Bacterial population, prepared culture suspension is serially diluted and spread on the agar plate. The plate's are incubated at 37ºC for 24 hours after spreading on the agar plates.

The number of colonies is then counted and the concentration of organisms is given by the following equation:

$$\frac{CFU}{mL} = \frac{n*d}{V} \quad (1)$$

Where n=no of colony forming units (CFU's).

d=dilution factor.

V=volume of spread=100 µl (for all organisms)

Table-2 shows the average CFU/mL for each micro-organism. (Only countable colonies considered which are greater than 30 or less than 300).

TABLE 2

Bacterial concentration in Stock Culture

| Micro-organism Used | Staphylococcus Aureus | Escherichia Coli |
|---|---|---|
| Dilutions | $10^4$ | $10^3$ |
| 1 | 299 | 42 |
| 2 | 289 | 57 |
| 3 | 294 | 52 |
| AVG CFU #n | 294 | 50.33 |
| CFU/ml as per equation −1 | $2.94 \times 10^7$ | $5.03 \times 10^5$ |

2. Qualitative Determination of Bacterial Load on Yarns:

1 mL of above culture suspension is taken in 2 mL of centrifuge tube. The yarn samples to be tested are cut in to the length of 10 cm each (triplicate). The yarn sample is added in 2 mL centrifuge tube and allowed it to incubate for 30 minutes at 37° C. Treated yarn is taken out with the help of sterile tweezers and air dried in a sterile environment for 1 minute.

The yarn is then placed on the nutrient agar plate and allowed to stick to it. Agar plates are incubated for 24 hours at 37° C.

TABLE 3

Qualitative growth of micro-organisms on treated and untreated yarn

| Samples | Growth | No Growth |
|---|---|---|
| *Staphylococcus Aureus* | | |
| Treated yarn | | − |
| Untreated yarn | +++++ | |
| *Escherichia Coli* | | |
| Treated yarn | | − |
| Untreated yarn | +++++ | | where '+++++' shows the colonies numerous to count and '++' shows few colonies but not numerous. '−' shows no growth at all.

As shown in FIG. 8, it is observed that *Staphylococcus Aureus* and *Escherichia coli* does not grow at all after the copper oxide coating on the surface of the yarn.

3. To Determine the Effect of Antimicrobial Yarns in Remaining Bacterial Culture:

1 ml of above culture suspension is taken in 2 ml of centrifuge tube. Yarn samples to be tested are cut into the length of 10 cm each (triplicate The yarn sample is added in 2 mL centrifuge tube and allowed it to incubate for 30 minutes at 37° C. Treated yarn is taken out with the help of sterile tweezers and air dried in a sterile environment for 1 minute. After the removal of yarn, 1 ml of remaining culture is taken for serial dilution to $10^3$. The 100 µL of remaining solution is spread on a sterile agar plate. Incubation is done for 24 hours at 37° ° C.

It was observed that both types bacteria was not present in the culture. The FIG. 9 and FIG. 10 confirms that the culture in which uncoated yarn was added shows presence of bacteria while the culture in which coated yarn was added shows no bacteria.

Example 5: Anti-Viral Testing of Coated Material

In order to test Anti-viral properties of the coating the fabric material made up of polypropylene was coated using plasma based sputtering technique. The polypropylene material is generally used as filter material in the fabrication of N-95 mask. The 100 nm thin copper oxide coating was prepared and then tested for antiviral testing using SARS- Cov-2 virus. The viral RNA was extracted from the sample by using viral/pathogen extraction kit. Then qRT-PCR method was used to determine the Ct value. The number of viral particles were calculated using regression equation and Ct values. The tests were conducted after exposing the virus for 05 minute to both coated and uncoated surface.

The FIG. 11 shows the Number of viral particles and percentage viral reduction for uncoated and coated samples. The coated sample shows almost 98% viral reduction.

We claim:

1. A cylindrical magnetron sputtering assembly for coating on a flexible polymeric substrates with an antimicrobial material, said assembly comprising a sputtering setup and a cylindrical magnetron assembly;

said cylindrical magnetron assembly being mounted in said sputtering setup; wherein said cylindrical magnetron assembly comprises:

at least one cylindrical anode with plurality of slots mounted on a top base plate;

at least one central target cylindrical cathode positioned at the center of said anode;

a mechanical assembly for moving plurality of said flexible polymeric substrates; said mechanical assembly comprising at least one winder, at least one unwinder, plurality of pulleys and plurality of motors;

said sputtering setup comprising plurality of magnetic field coils, vacuum chamber and plurality of power supply, wherein the plurality of magnetic field coils are positioned outside the vacuum chamber; and wherein the plurality of slots are configured to pass the flexible polymeric substrates in a vertical direction.

2. The cylindrical magnetron sputtering assembly as claimed in claim 1, wherein said flexible polymeric substrates is selected from the group consisting of fabric, yarn, polymeric filter media substrates, polypropylene, polystyrene, polyethylene, cotton and combinations thereof.

3. The cylindrical magnetron sputtering assembly as claimed in claim 2, wherein said assembly coats moving fabric or moving yarn with said antimicrobial material.

4. The cylindrical magnetron sputtering assembly as claimed in claim 3, wherein said mechanical assembly moves said fabric in vertical direction or said yarn in horizontal direction.

5. The cylindrical magnetron sputtering assembly as claimed in claim 3 wherein said antimicrobial material is uniformly coated with a thickness of 50-100 nm on said yarn or said fabric.

6. The cylindrical magnetron sputtering assembly as claimed in claim 1, wherein said antimicrobial material is copper, zinc, or titanium.

7. The cylindrical magnetron sputtering assembly as claimed in claim 1, wherein said antimicrobial material is nano copper oxide.

8. The cylindrical magnetron sputtering assembly as claimed in claim 1, wherein said assembly operates in vacuum at $10^{-2}$ mbar to $10^{-1}$ mbar and in combination with a DC power supply of −600 to −800 Volts under gas environment.

9. The cylindrical magnetron sputtering assembly as claimed in claim 2, wherein said fabric coated with said antimicrobial material is used as clothing, surgical garments, dressings, or bandages.

10. The cylindrical magnetron sputtering assembly as claimed in claim 2, wherein said yarn coated with said antimicrobial material is used as fabric, medical bandages, dressing gauges, or antimicrobial filters.

11. The cylindrical magnetron sputtering assembly as claimed in claim 2, wherein said polymeric filter media substrate is used for air purification, water purification, or combinations thereof.

12. A process for producing antimicrobial coating on a flexible polymeric substrates by the cylindrical magnetron sputtering assembly as claimed in claim 1, said process comprising the steps of:

a) generating a low pressure plasma in the cylindrical anode to sputter out an antimicrobial material from the target cylindrical cathode, b) generating magnetic field by said magnetic field coils to increase electron density for sputtering, c) performing an unwinding and a winding spool mechanism with said motors inside said vacuum chamber, and d) moving said flexible polymeric substrates multiple times through said cylindrical magnetron assembly to deposit a coating of said antimicrobial material of thickness of 50-100 nm.

13. The process as claimed in claim 12, wherein said flexible polymeric substrates is selected from the group consisting of fabric, yarn, polymeric filter media substrates, polypropylene, polystyrene, polyethylene, cotton and combinations thereof.

14. The process as claimed in claim 12, wherein said antimicrobial material is copper, Zinc, or Titanium.

15. The process as claimed in claim 12, wherein said antimicrobial material is nano copper oxide.

16. The process as claimed in claim 12, wherein said coating is performed in vacuum at $10^{-2}$ mbar to $10^{-1}$ mbar and in combination with a DC power supply of −600 to −800 Volts under gas environment.

17. The cylindrical magnetron sputtering assembly as claimed in claim 3, wherein said moving fabric is woven or non-woven.

18. The cylindrical magnetron sputtering assembly as claimed in claim 1, wherein said flexible polymeric substrates is fabric, yarn, or combinations thereof.

19. The cylindrical magnetron sputtering assembly as claimed in claim 8, wherein said gas environment is argon or oxygen.

20. The process as claimed in claim 16, wherein said gas environment is argon or oxygen.

* * * * *